CACTACEAE PLANT FAMILY

Filed March 13, 1973 2 Sheets-Sheet 1

United States Patent Office

Plant Pat. 3,574
Patented June 18, 1974

3,574
CACTACEAE PLANT FAMILY

Barnell L. Cobia, Winter Garden, Fla., assignor to
B. L. Cobia, Inc., Winter Garden, Fla.

Filed Mar. 13, 1973, Ser. No. 340,931
Int. Cl. A01h 5/00
U.S. Cl. Plt.—88 1 Claim

ABSTRACT OF THE DISCLOSURE

A new and distinct hybrid plant variety of the Cactaceae family obtained through cross-pollination of a plant of the *Zygocactus truncatus* "Delicatus" variety and a *Zygocactus truncatus* variety known commercially as "Christmas Cheer" is principally distinguished from its parents and known related varieties by a growth habit that combines a fast growth rate, an upright and compact appearance, thin cladophylls with from 6 to 9 teeth per cladophyll, and a flower having a small ovary with a high sterility factor, a bloom with translucent white perianth tube forming and laminating tepals, a carina which is clearly demarcated by its color, and a bloom life of from about 6 to about 8 days.

The invention relates to a new and distinct plant variety of the Cactaceae family and which has been named the *Zygocactus truncatus* "Alba" by the inventor.

Certain plants of the Cactaceae family are well known in the foliage plant market and among these are those of the *Zygocactus truncatus* "Delicatus" variety and a *Zygocactus truncatus* variety commonly known as the "Christmas Cheer" variety. These varieties tend to bloom in the months of November and December in the northern hemisphere and are found in the foliage plant retail market area during the Thanksgiving and Christmas seasons.

The "Delicatus" variety has translucent white tepals but the bloom life is relatively short being in the area of about two days. Because of this its acceptance by merchants at the retail level of sales is limited. Growers are also reluctant to grow the variety because of delays in transportation to the market areas and the large costs that are involved in manually selecting plants for shipment which are at the proper stage of budding to provide reasonable assurance of mature blooming when the plants reach their destination.

The variety commonly known as "Christmas Cheer" has a bloom life in the area of from about five to eight days but has a bloom with tepals that are salmon colored. This color is less appealing to the general public during the Thanksgiving-Christmas season and hence there is a need for a *Zygocactus truncatus* variety that has a white bloom and also a bloom life which provides a suitable shelf life at the retail level of sales.

A general object of the invention has been to develop a variety of the Cactaceae family which may be considered as having a white bloom and a relatively long bloom life. Yet another object of the invention has been to develop a variety having the foregoing general objective and which is faster growing and more compact in appearance than the two varieties heretofore mentioned.

The objectives of the invention have been fully realized by the development of the new plant variety hereinafter described in detail. The new plant variety was developed in a nursery located at Winter Garden, Fla., as a hybrid secured by cross-pollinating the flower of a plant of the *Zygocactus truncatus* "Delicatus" variety with pollen from a plant of the *Zygocactus truncatus* variety commonly known as "Christmas Cheer." The seeds taken from the fertilized seed pod of the "Delicatus" variety were cultivated at the mentioned nursery location by the inventor and after prolonged observation of the seedlings the hybridized plant of the new plant variety was selected and asexually reproduced by the inventor at the Winter Garden nursery by the propagation of stem cuttings taken from the original hybrid plant.

Through successive propagations, it has been ascertained that plants of the new variety generally resemble the parent varieties but are distinguishable from the parent varieties and from other related varieties known to the inventor by a growth habit which is evident in plants propagated and grown under nursery conditions utilized in the growing of tropical plants at Winter Garden, Fla., as combining the following principal characteristics:

1. A faster growth rate than its parents,
2. A more upright and compact (denser) appearance than its parents, as evidenced by more erect stems with heavier (more frequent) branching,
3. Thinner cladophylls than its parents and with from 6 to 9 teeth that are generally longer than its parents, and
4. A flower having
   (a) an ovary with a high sterility factor and which is smaller in size than its parents, and
   (b) a bloom with a life from about six to about eight days, translucent white perianth tube forming and laminating tepals, and a carina which is clearly demarcated by its color.

The accompanying drawings serve, by color photographic means, to illustrate the new plant variety and wherein.

Figure 1:
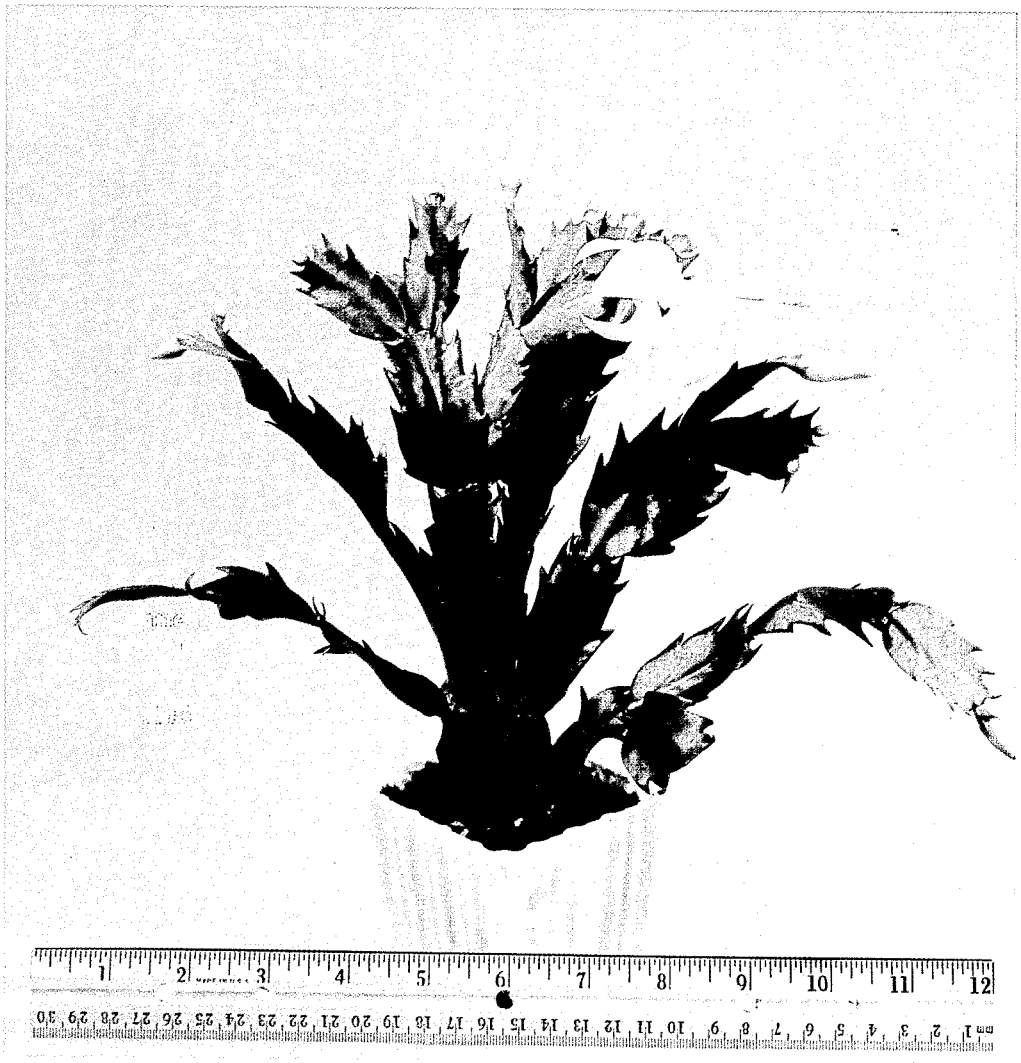
FIG. 1 is a color photograph of a plant specimen of the new plant variety.
Figure 2:
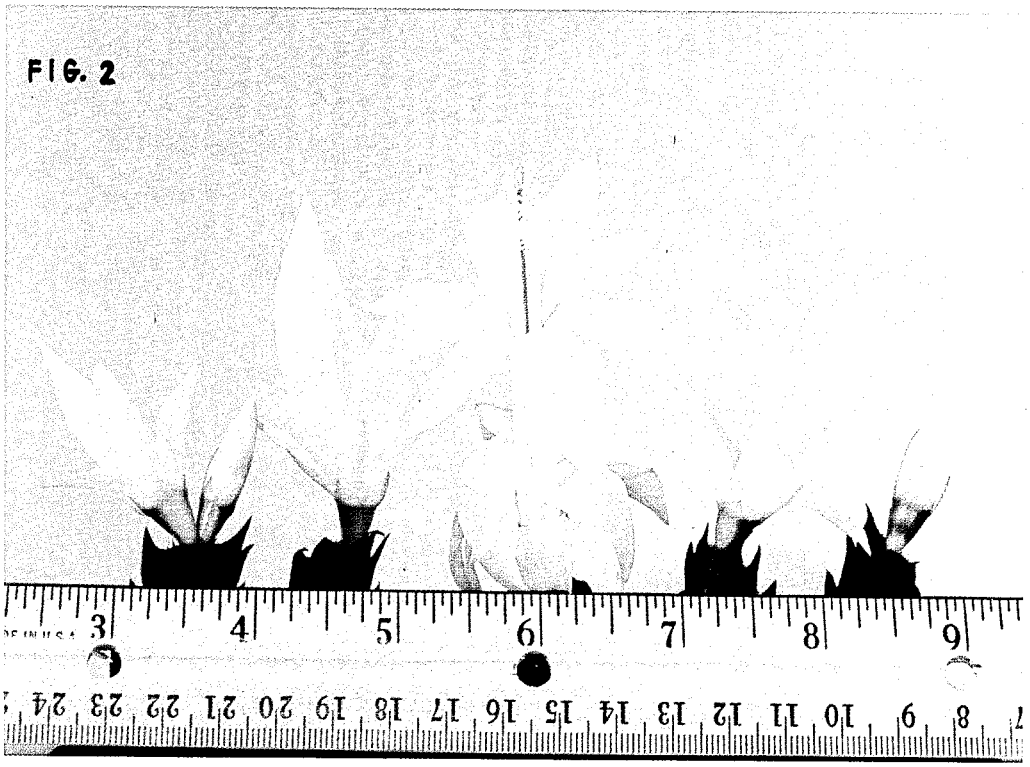
FIG. 2 is a color photograph showing a fully opened bloom of the new variety together with several buds of the new variety in various stages of bloom maturity.
Figure 3:
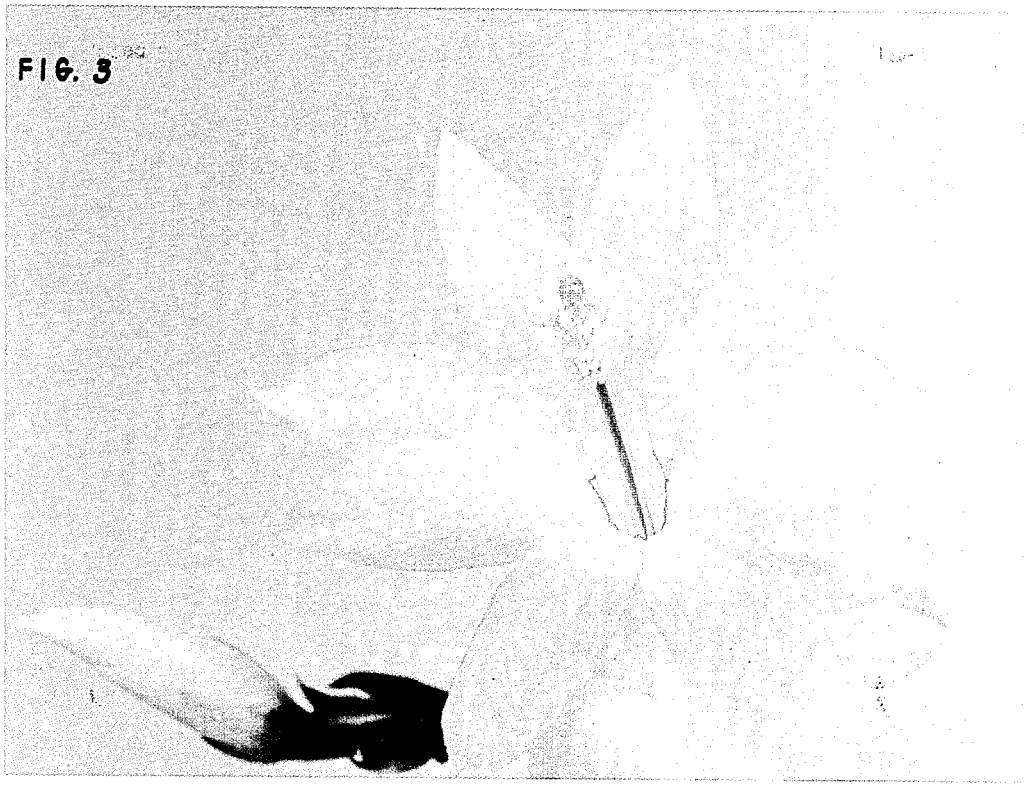
FIG. 3 is another color photograph of a fully open bloom as seen when looking into the throat of the perianth tube.

The following is a detailed description of the new plant variety with colors and hues, unless otherwise clearly indicated by the text through the absence of color notations, being named in accord with the ISCC-NBS method of designating colors (U.S. Department of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md. The following description is further based on observations of well fertilized plants of less than one year of age from initial propagation and which were grown under 50–70% shaded glass-house nursery conditions in the Winter Garden, Florida area and wherein temperatures range from 60 to 85° during the winter months, from 75 to 95° F. during the summer months and are ambient during intervening periods.

DETAILED PLANT DESCRIPTION

Name: *Zygocactus truncatus* "Alba."

Parentage:

A. *Maternal.—Zygocactus truncatus* "Delicatus."

B. *Paternal.—Zygocactus truncatus* variety known commercially as "Christmas Cheer."

Classification:

A. Botanic (Britton and Rose, *The Cactaceae*, Constable and Co., Ltd., London 1937, Vol. IV)—

(1) Family: Cactaceae
(2) Tribe: *Cereeae*
(3) Sub-tribe: *Epiphyllanae*
(4) Genus: *Zygocactus*
(5) Species: *truncatus* (Haworth) Schumann B. Commercial—Thanksgiving — Christmas blooming cactus.

Form: Terrestrial, shade-loving, succulent, leafless plant with jointed and branched stems.

Stems:

A. *General.*—Irregular with usually multi-chotomous branching of both upright and pendulous, adventiously rootable, flattened cladophylls that have a prominent midrib and prominently toothed lateral wings.

B. *Cladophylls.*—

(1) General—Elongated and flat with transversely elongated, areole bearing, truncated apex, with inwardly tapering basal wing margins that merge through a broad usually pointed basal juncture with the cladophyll therebelow, with an axillary areole associated with each tooth, and with some tendency for wings to curl.

(2) Midrib—(a) General—Extends longitudinally of cladophyll and continuously through joints with laterally tapering cortex at wing insertions. Pith surrounding vascular bundles that branch and provide lateral extensions of the vascular system to marginal teeth. (b) texture—Smooth waxy epidermis with wax in small embedded scales and becoming corky in basal stem areas with age. (c). Size (2–6 mos. old)—(1) Length: Usually between 20 and 60 mm. (2) Thickness: Usually between 1 and 7 mm. (d) Color (at maturity)—Commonly moderate yellow green (7.5 GY 5/4) (7.5 GY 5/6) and/or moderate olive green (7.5 GY 4/4) (7.5 GY 4/6).

(3) Wings—(a) General shape—Generally flattened from midrib cortex to tooth insertions with tendency to curl. (b) Margins—Toothed (modified leaves). (c) Texture—Succulent to leathery with smooth waxy epidermis having wax arranged in small embedded scales and becoming corky in basal plant areas with age. (d) Size (2–6 mos. old)—(1) Center thickness—Usually between 1.0 and 2.5 mm. (2) Width (as measured from cladophyll axis to most offset lateral areole)—Usually between 7 and 16 mm. (e) Color (at maturity)—Commonly moderate yellow green (7.5 GY 5/4 (7.5 GY 5/6) and/or moderate olive green (7.5 GY 4/4) (7.5 GY 4/6).

(4) Teeth—(a) General shape—Generally flattened and tapered along margins from wing insertions to an apex having a hyaline, single cell, pointed spine with nonpredictable bending, and with irregular adaxial and abaxial marginal curvatures. (b) Orientation—Usually projects generally distally of cladophyll base with the median of the tooth angles (as measured at the distal side of the intersect with the cladophyll axis of a line through the tooth apex and the midpoint between the abaxial and adaxial areoles thereof) formed by non-basal teeth of a cladophyll usually being between 12° and 24°. (c) Margins—Entire. (d) Texture—Succulent to leathery with smooth waxy epidermis having wax in small embedded scales and becoming corky in basal plant areas with age. (e) Number—Usually from 6 to 9 and commonly 8 per cladophyll. (f) Size (2–6 mos. old)—(1) Center thickness: Usually between 0.5 and 1.3 mm. (2) Aerole to apex dimension (adaxial marginal side): Usually between 1 and 12 mm. (g) Color (at maturity)—Commonly moderate yellow green (7.5 GY 5/4) (7.5 GY 5/6) and/or moderate olive green (7.5 GY 4/4) (7.5 GY 4/6).

(5) Areoles—(a) Terminal areole—Large elongated oval-shaped with several acicular bristles, copious multicellular hairs, and several buds that may mature into either new cladophylls or flowers. The opposite ends of the areole are located adjacent to subsidiary areoles which are in turn located at the axils of teeth that are located at the distal end of cladophyll. (b) Auxiliary areoles—Acicular bristles without glochidia but having copious, short, brownish to colorless, multicellular hairs. In areoles that are located below the teeth at the distal end of the cladophyll, there is usually only one bud that is frequently latent.

Buds: Unarmored, ovoid and chlorophyllous.

Flowers:

A. *General.*—Sessile, zygomorphic, usually solitary, terminal, perfect, and epigynous with double hypanthium and tepals (undifferentiated whorled sepals and petals) having a spiral emergence as a perianth provided with a sepaloid series of free tepals, a tube laminating series of tepals, and a tube forming series of united tepals.

B. *Sepaloid series.*—(1) General: Free tepals inserted on top of ovary. (2) Shape: Tapered from insertion to apex in outer members of whorl and grading inwardly in the whorl to provide progressively broader apices and longer base-tip dimensions. All members have pointed tip and entire margins with sparse irregular teeth appearing mainly in apex areas of the inner members of the whorl. (3) Texture: Succulent and glabrous outer whorl members and grading inwardly in the whorl to silken blades with fleshy basal areas. (4) Number: Usually from 4 to 6. (5) Size (at full bloom): (a) Base-tip dimension—Usually less than 15 mm. (b) Maximum width dimension—Usually less than 12 mm. (6) Color: Yellow green hue fading inwardly in the whorl in the marginal areas to a translucent white. Commonly strong yellow green (2.5 GY 6/8) (2.5 GY 7/8 (5 GY 7/8), brilliant yellow green (2.5 GY 8/8) and/or moderate yellow green (2.5 GY 7/6) (5 GY 7/6) in outer members of the whorl with light yellow green (2.5 GY 8/6) (2.5 GY 9/4) (2.5 GY 9/6) (5 GY 8/6) (5 GY 9/4) along axis and a translucent white along margins of the inner members of the whorl. (7) Orientation at full bloom: Varying inwardly in the whorl from erect to recurve.

C. *Tube laminating series.*—(1) General: Inserted on ovary and basally united below the throat as outer laminations on the perianth tube and with progressively greater amounts of basal fusion inwardly in the whorl. (2) Shape: Grading inwardly in whorl with progressively longer base-tip dimensions and progressively broader apices so that blade area changes from ovate inwardly to spactulate with acute tips. Entire margins with sparse irregular teeth mainly in apex areas. (3) Texture: Succulent, slightly fleshy, basal areas with silken blades. (4) Number: Usually 5 to 7. (5) Size (at full bloom):

(a) Base-tip dimensions—Usually between 20 and 60 mm.

(b) Maximum width dimensions—Usually between 12 and 17 mm.

(6) Color: A translucent white. (7) Orientation at full bloom: Upright to recurved.

D. *Tube forming series.*—(1) General: Basally united to form hollow perianth tube that is inserted on ovary and equipped with irregular carina (keel) at throat. (2) Shape:

(a) Perianth tube—Elongated, and ellipsoidal in cross section with major ellipsoidal axis arranged generally perpendicular to general plane of cladophyll.

(b) Blades—Nearly zygomorphic, thin spatulate with acute tip. Entire margins with sparse, irregular teeth mainly in apex area.

(c) Carina (keel)—Irregular and transending.

(3) Texture:

(a) Perianth tube—Thick, succulent and slightly ribbed.

(b) Blades—Translucent and silken.

(c) Carina (keel)—Fleshy.

(4) Blade number: Usually 8. (5) Size (at full bloom):

(a) Perianth tube—(1) Base to keel length: Usually between 30 and 40 mm. (2) Internal major axis (at throat): Usually between 8 and 11 mm. when measured perpendicular to axis of perianth tube. (3) Internal minor axis (at throat): Usually between 6 and 8 mm. when measured perpendicular to axis of perianth tube.

(b) Blades—(1) Length (keel to tip): Usually between 25 and 45 mm. (2) Width (maximum): Usually between 5 and 15 mm.

(6) Color (at full bloom):

(a) Perianth tube—A translucent white.

(b) Blades—A translucent white.

(c) Carina (keel)—Typically moderate purplish red (2.5 RP 4/10) (5 RP 5/10), dark purplish pink (5 RP 6/8), deep purplish pink (5 RP 6/10) and/or strong reddish purple (2.5 RP 5/10).

(7) Orientation at full bloom: Erect to recurve.

E. Androecium (stamens).—(1) General—Numerous exserted and diadelphous stamens with one group having filaments basally fused to the perianth tube and the other group having filaments basally united to form a nectary housing, thin annulus around the style and which is provided with a thin, deflexed, irregularly toothed margin or ruffle at the throat of the annulus. (2) Stamen number—

(a) Tube attached group: Usually from 86 to 92.

(b) Basally united group: Usually from 20 to 23.

(3) Filament—

(a) General: Translucent and glabrous with anther connective.

(b) Shape: Long, slender and gradually tapering from base to anther connective.

(c) Texture: Glabrous and silken.

(d) Color: A translucent white.

(e) Size (at full bloom): (1) Length—(a) Tube attached group: Usually 42 to 62 mm. (b) Basally united group: Usually from 44 to 57 mm. (2) Diameter—Usually between 0.3 and 0.4 mm. intermediate the opposite ends.

(4) Anthers—

(a) General: Adnate with four longitudinally dehiscent pollen sacs.

(b) Shape: Elongated.

(c) Texture: Waxy.

(d) Color (before dehiscing): Usually pale yellow (5 Y 9/4) and/or pale yellowish green (7.5 Y 9/4).

(e) Size: Usually 1.2 to 2.1 mm. in length.

(f) Sterility: Usually between 7 and 21%.

F. *Gynoecium* (*pistil*).—(1) General—Compound, parietal placentation with united style surrounded by annular diffuse nectary at its insertion. (2) Style—

(a) General: Hollow, stout and inserted in ovary.

(b) Shape: Elongated, cylindrical and generally tapering.

(c) Texture: Fleshy and glabrous with short inner glutinous hairs at distal end.

(d) Color: Usually strong reddish purple (near 10 P 5/10) (2.5 RP 5/10), moderate purplish red (5 RP 5/10), and/or light reddish purple (2.5 RP 6/8).

(e) Size (at full bloom): (1) Length—Usually between 61 and 72 mm. (2) Diameter—Usually varies from about 0.5 to about 1 mm.

(3) Stigma—

(a) General: Exserted and erect with usually from 6 to 9 inner marginally adhering lobes.

(b) Shape: Elongated and tapering toward lobe tips and having relatively blunt apices.

(c) Texture: Fleshy and smooth with short glutinous hairs.

(d) Color: Usually strong reddish purple (2.5 RP 5/10) and deep purplish pink (near 5 RP 6/10).

(e) Size (lobe length at full bloom): Usually from 4 to 6 mm. along inner margins.

(4) Ovary—

(a) General: Epigynous with thin epidermis and distally located concavity and with single cavity having from 6 to 9 carpels commonly devoid of ovules.

(b) Shape: Terete to ovoid and generally broadening from insertion to floral end.

(c) Texture: Succulent and glabrous with thin outer epidermis.

(d) Color: Usually moderate yellow green (2.5 Gy 7/6) (5 GY 7/6) (5 GY 6/6).

(e) Size (at full bloom): (1) Length (insertion to concavity base)—Usually between 4 and 12 mm. (2) Major axis (distal end of concavity—Usually between 2.0 and 5.5 mm.

(f) Sterility factor: Usually more than 80%.

Fruit: Data unavailable because of sterility.

Growing characteristics: A fast growth rate with the production of more than 1.5 times the number of mature cladophylls during comparable growing periods than either parent, a more upright and compact (denser) apparance than its parents, as evidenced by more erect stems with heavier (more frequent) branching, a greater resistance than its parents to nutrient deficiencies, and a bloom life (from initial tepal separation to initial tepal withering) of from about 6 to about 8 days.

The following is a general description of a specimen of the new plant variety that was grown from the propagation of a single cladophyll in a nursery at Winter Garden, Fla.

Age of plant: 10 months from initial propagation.
Branches from propagated cutting: 3.
Total number of cladophylls grown from cutting: 33.
General:

| Branch No. | Number of cladophylls | Max. length, mm. | Number of tips |
|---|---|---|---|
| 1 | 13 | 190 | 9 |
| 2 | 11 | 146 | 7 |
| 3 | 9 | 146 | 5 |

Midribs:

| Branch No. | Length (avg.) mm. | Thickness (avg.), mm. |
|---|---|---|
| 1 | 45.5 | 3.34 |
| 2 | 42.0 | 3.28 |
| 3 | 41.9 | 3.19 |

Wings:

| Branch No. | Center thickness (avg.), mm. | Max. width (avg.), mm. |
|---|---|---|
| 1 | 1.69 | 12.8 |
| 2 | 1.83 | 10.5 |
| 3 | 1.72 | 11.2 |

Teeth:

| Branch No. | Number cladophylls (avg.) | Center thickness (avg.), mm. | Areole to apex dimension (avg.), mm. | Tooth angle (median) deg. |
|---|---|---|---|---|
| 1 | 7.9 | 1.05 | 6.1 | 14.7 |
| 2 | 8.9 | .98 | 5.6 | 16.4 |
| 3 | 7.7 | .94 | 6.3 | 15.3 |

Cladophyll color: Moderate yellow green (7.5 GY 5/4), moderate olive green (7.5 GY 4/6).

The following is a general description of a flower of the new plant variety which bloomed in November on a plant grown under shaded glasshouse nursery conditions in Winter Garden, Fla.

Bloom life: 7 days.

Sepaloid series of tepals:

(1) *Number*—6.

(2) *Size (at full bloom)*—(a) Maximum base-tip dimension—14 mm. (b) Minimum base-tip dimension—1 mm. (c) Maximum width dimension—11 mm.

(3) *Color.*—Strong yellow green (2.5 GY 6/8) (2.5 GY 7/8) in outer whorl members. Light yellow green (2.5 GY 9/6) (5 GY 9/4) along axis of inner whorl members and fading to a translucent white along the margins thereof.

Tube laminating series:

(1) *Number*—6.

(2) *Size (at full bloom).*—(a) Maximum base-tip dimension—53 mm. (b) Minimum base-tip dimension—22 mm. (c) Maximum width dimension—16 mm. (d) Minimum width dimension—14 mm.

(3) *Color.*—A translucent white.

Tube forming series of tepals:

(1) *Number*—8.

(2) *Size (at full bloom).*—

(a) Perianth tube—(1) Base keel length—36 mm. (2) Interior major axis (at throat)—9 mm. (3) Interior minor axis (at throat)—6 mm.

(b) Blades—(1) Maximum length (keel to tip)—38 mm. (2) Minimum length (keel to tip)—31 mm. (3) Maximum width—14 mm. (4) Minimum width—10 mm.

(3) *Color.*—

(a) Perianth tube—A translucent white.

(b) Blades—A translucent white.

(c) Carina (keel)—Deep purplish pink (5 RP 6/10).

Androecium:

(1) *Stamen number.*—

(a) Tube attached group—89.

(b) Basally united group—23.

(2) *Filaments.*—

(a) Color—A translucent white.

(b) Size (at full bloom)—(1) Length—(a) Tube attached group: 56 mm. (avg.). (b) Basally united group: 52 mm. (avg.). (2) Diameter—About .36 mm. intermediate the opposite ends.

(3) *Anthers.*—

(a) Color (before dehiscing)—Pale yellowish green (7.5 Y 9/4).

(b) Size—1.8 mm. (avg.).

(c) Sterility factor—15%.

Gynoecium (pistil):

(1) *Style*—

(a) Color—Moderate purplish red (5 RP 5/10).

(b) Size (at full bloom)—(1) Length—66 mm. (2) Diameter—Varies from .5 to 1 mm.

(2) *Stigma.*—

(a) Color—Deep purplish pink (near 5 RP 6/10).

(b) Size (lobe length)—5 mm.

(3) *Ovary*—

(a) Color—Moderate yellow green (5 GY 7/6).

(b) Size (at full bloom)—(1) Length (insertion to concavity base)—9 mm. (2) Major axis (distal end of concavity)—5 mm. (3) Minor axis (distal end of concavity)—3.0 mm.

(c) Sterility factor—100%.

I claim:

1. The new and distinct hybrid plant variety of the Cactaceae family as described and illustrated and which is principally distinguished by a growth habit that combines the following characteristics:

(1) A faster growth rate than its parents, (2) A more upright and compact appearance than its parents, (3) Thinner cladophylls than its parents and with from 6 to 9 teeth that are generally longer than its parents, and (4) A flower having (a) an ovary with a high sterility factor and which is smaller in size than its parents, and (b) a bloom with a lift from about 6 to about 8 days, translucent white perianth tube forming and laminating tepals, and a carina which is clearly demarcated by its color.

No references cited.

ROBERT E. BAGWILL, Primary Examiner

PO-1050
(5/69)

UNITED STATES PATENT OFFICE
CERTIFICATE OF CORRECTION

Plant Patent No. 3574 Dated June 18, 1974

Inventor(s) Barnell L. Cobia

It is certified that error appears in the above-identified patent and that said Letters Patent are hereby corrected as shown below:

Column 3, Lines 7 & 8, delete "adventiously" and substitute -- adventitiously --;
Line 48, delete "(7.5 GY 5/4" and substitute -- (7.5 GY 5/4) --;
Column 4, Line 11, delete "Auxiliary" and substitute -- Axillary --;
Line 45, delete "(2.5 GY 7/8" and substitute -- (2.5 GY 7/8) --;
Column 6, Line 43, delete "Usually between 2.0 and 5.5 mm." and substitute -- Usually between 4 and 9 mm. (3) Minor Axis (distal end of concavity) - Usually between 2.0 and 5.5 mm.--;
Lines 50 & 51, delete "apparance" and substitute -- appearance --;
Column 7, Line 15, cancel "8.9" and substitute -- 8.0 --;
Line 47, delete "Base keel" and substitute -- Base to keel --;

Signed and sealed this 29th day of October 1974.

(SEAL)
Attest:

McCOY M. GIBSON JR.
Attesting Officer

C. MARSHALL DANN
Commissioner of Patents